United States Patent [19]

Butina et al.

[11] Patent Number: 4,894,387

[45] Date of Patent: Jan. 16, 1990

[54] 5-SUBSTITUTED-3-AMINOALKYL INDOLE DERIVATIVES

[75] Inventors: Darko Butina, Arlesey; Michael D. Dowle, Ware; Ian H. Coates, Pertford, all of England

[73] Assignee: Glaxo Group Limited, London, England

[21] Appl. No.: 30,235

[22] Filed: Mar. 26, 1987

Related U.S. Application Data

[63] Continuation of Ser. No. 679,029, Dec. 6, 1984, abandoned.

[30] Foreign Application Priority Data

Dec. 6, 1983 [GB] United Kingdom ................ 8332437

[51] Int. Cl.⁴ ..................... A61K 31/40; C07D 209/14
[52] U.S. Cl. .................................. 514/415; 548/504; 548/505; 548/506
[58] Field of Search ................ 514/415; 548/504, 506, 548/505

[56] References Cited

U.S. PATENT DOCUMENTS

4,785,016 11/1988 Evans ................................... 514/415
4,816,470 3/1989 Dowle ................................... 514/415

FOREIGN PATENT DOCUMENTS

895430 5/1962 United Kingdom .
2035310 6/1980 United Kingdom .
2083463 3/1982 United Kingdom .
2124210 2/1984 United Kingdom .

OTHER PUBLICATIONS

Handbook of Experimental Pharmacology, vol. XIX, Springer-Verlag, New York, 1966.
A Manual of Pharmacology, Sollmann, 8th Ed., pp. 45–57.
Proposals for the Classification and Nomenclature of Functional Receptors and 5-Hydroxytryptamine, Neuropharmacology, vol. 25, No. 6, pp. 563–576, 1986.
Pharmacological Principles and Practice, Paton, pp. 1–2.
The Pharmacological Basis of Therapeutics, 7th Ed., pp. 35–37.
Evidence for Two Types of Excitatory Receptor for 5-Hydroxytryptamine in Dog Isolated Vasculature, Apperley, pp. 215–223, Re J. Pharmac, (1980).

Primary Examiner—Mark L. Berch
Attorney, Agent, or Firm—Bacon & Thomas

[57] ABSTRACT

Compounds are disclosed of the general formula (I)

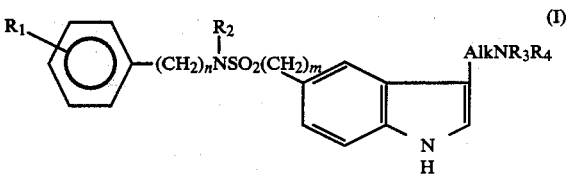

wherein
$R_1$ represents halogen, alkyl, alkoxy or hydroxyl, or a group $NR_aR_b$ or $CON_aR_b$, where $R_a$ and $R_b$ are hydrogen, alkyl or alkenyl or with the nitrogen atom form a saturated monocyclic 5 to 7-membered ring;
$R_2$ represents hydrogen or alkyl;
$R_3$ and $R_4$ represent hydrogen, $C_{1-3}$ alkyl or propenyl or $R_3$ and $R_4$ together form an aralkylidene group;
Alk represents a $C_{2-3}$ alkylene chain;
n and m, are integers of 1 to 4 or n is zero, and their physiologically acceptable salts and solvates.

The compounds are described as useful in treating pain originating from dilatation of the cranial vasculature in particular migraine and cluster headache and can be formulated in conventional manner as pharmaceutical compositions with carriers or excipients for administration by any convenient route.

9 Claims, No Drawings

5-SUBSTITUTED-3-AMINOALKYL INDOLE DERIVATIVES

This application is a continuation of application Ser. No. 679,029 filed Dec. 6, 1984, abandoned.

This invention relates to indole derivatives, to processes for their preparation, to pharmaceutical compositions containing them and to their medical use, in particular to compounds and compositions of use in the treatment of migraine.

The pain of migraine is recognised as being primarily of vascular origin, caused by excessive dilatation of the cranial vasculature. Known treatments for migraine include the administration of compounds having vasoconstrictor properties such as ergotamine. However, ergotamine is a non-selective vasoconstrictor which constricts blood vessels throughout the body and has undesirable and potentially dangerous side effects. Migraine may also be treated by administering an analgesic usually in combination with an antiemetic but such treatments are of limited value.

There is thus a need for a safe and effective drug for the treatment of migraine, which can be used either prophylactically or to alleviate an established headache, and a compound having a selective vasoconstrictor activity would fulfill such a role.

We have now found a group of indole derivatives having potent and selective vasoconstrictor activity.

The present invention provides an indole of the general formula (I):

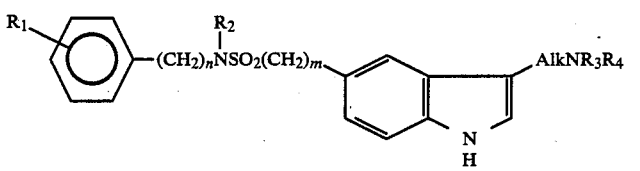

wherein $R_1$ (which may be in the ortho, meta or para position) represents a halogen atom or an alkyl, alkoxy or hydroxyl group, or a group $NR_aR_b$ or $CONR_aR_b$, where $R_a$ and $R_b$, which may be the same or different, each represents a hydrogen atom or an alkyl or alkenyl group, or together with the nitrogen atom to which they are attached form a saturated monocyclic 5 to 7-membered ring which may contain an additional hetero function, for example, an oxygen atom or the group $NR_5$ (where $R_5$ is a hydrogen atom or a lower alkyl group);

$R_2$ represents a hydrogen atom or a $C_{1-3}$ alkyl group;

$R_3$ and $R_4$, which may be the same or different, each represents a hydrogen atom or a $C_{1-3}$ alkyl or propenyl group or $R_3$ and $R_4$ together form an aralkylidene group;

Alk represents an alkylene chain containing two or three carbon atoms which may be unsubstituted or substituted by not more than two $C_{1-3}$ alkyl groups; and n and m, which may be the same or different, each represents an integer from 1 to 4 or n may be zero, and physiologically acceptable salts and solvates (e.g. hydrates) thereof.

The invention includes within its scope all optical isomers of compounds of general formula (I) and their mixtures including the racemic mixtures thereof.

Referring to the general formula (I), the alkyl groups and alkyl moiety of the alkoxy groups in the general formula (I) may be straight chain or branched chain alkyl groups containing 1 to 3 carbon atoms, examples of an alkyl group include methyl, ethyl, propyl and isopropyl groups. The alkenyl groups preferably contain 3 or 4 carbon atoms, examples of which include propenyl and butenyl groups. It will be appreciated that when $R_a$ is an alkenyl group the double bond must be separated from the nitrogen atom by at least one methylene group. When $R_1$ represents a halogen atom, this may be for example, a fluorine, chlorine or bromine atom. The aralkylidene group is preferably an aryl methylidene group such as benzylidene.

In the compounds of general formula (I), $R_1$ preferably represents a halogen atom, a $C_{1-3}$ alkyl or $C_{1-3}$ alkoxy group, or a group $NR_aR_b$ or $CONR_aR_b$, in which $R_a$ and $R_b$, wich may be the same or different each represents a hydrogen atom or a $C_{1-3}$ alkyl group.

$R_2$ is preferably a hydrogen atom.

$R_3$ and $R_4$, which may be the same or different preferably represent hydrogen atoms or $C_{1-3}$ alkyl or propenyl groups.

The group Alk in the compounds of formula (I) is preferably an unsubstituted alkylene chain containing two or three carbon atoms, especially an unsubstituted alkylene chain containing two carbon atoms. m is preferably 1 or 2.

A preferred class of compounds falling within the scope of general formula (I) is that represented by the general formula (Ia):

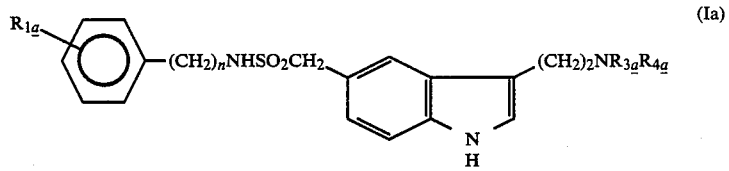

wherein $R_{1a}$ (which may be in the ortho, meta or para position) represents a $C_{1-3}$ alkoxy group e.g. methoxy, or a $C_{1-3}$ alkyl group e.g. methyl;

$R_{3a}$ and $R_{4a}$, which may be the same or different each represents a hydrogen atom or a $C_{1-3}$ alkyl group, e.g. methyl or ethyl; and n is an integer from 1 to 4;

and physiologically acceptable salts and solvates (e.g. hydrates) thereof.

In compounds of formula (Ia) it is preferred that the total number of carbon atoms in $R_{3a}$ and $R_{4a}$ does not exceed two, and most preferably $R_{3a}$ and $R_{4a}$ each represents a methyl group.

Preferred compounds according to the invention include:

3-(2-aminoethyl)-N-[(4-methoxyphenyl)methyl]-1H-indole-5-methanesulphonamide,

N-[(4-methoxyphenyl)methyl]-3-[2-(methylamino)ethyl]-1H-indole-5-methanesulphonamide, 3-(2-aminoethyl)-N-[(4-methoxyphenyl)ethyl]-1H-indole-5-methanesulphonamide, 3-(2-aminoethyl)-N-[3-(4-methoxyphenyl)propyl]-1H-indole-5-methanesulphonamide, and their physiologically acceptable salts and solvates.

A particularly preferred compound according to the invention is:

3-[2-(dimethylamino)ethyl]-N-[2-(4-methoxyphenyl)ethyl]-1H-indole-5-methansulphonamide and its physiologically acceptable salts and solvates.

Suitable physiologically acceptable salts of the indoles of general formula (I) include acid addition salts formed with organic or inorganic acids for example hydrochlorides, hydrobromides, sulphates, fumarates, maleates and succinates. Other salts may be useful in the preparation of the compounds of general formula (I) e.g. creatinine sulphate adducts and oxalates.

It will be appreciated that the invention extends to other physiologically acceptable equivalents of the compounds according to the invention, i.e. physiologically acceptable compounds which are converted in vivo into the parent compound. Examples of such equivalents include physiologically acceptable labile N-acyl derivatives such as the N-acetyl derivative.

Compounds of the invention selectively constrict the carotid arterial bed of the anaesthetised dog, whilst having a negligible effect on blood pressure. The selective vasoconstrictor action of compounds of the invention has been demonstrated in vitro.

Compounds of the invention are useful in treating pain originating from dilatation of the cranial vasculature, in particular migraine and cluster headache.

Accordingly the invention also provides a pharmaceutical composition adapted for use in medicine which comprises at least one compound of formula (I) or a physiologically acceptable salt or solvate (e.g. hydrate) thereof and which is formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation. Formulations of the compounds according to the invention for oral administration are preferred.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose; fillers (e.g. lactose, microcrystalline cellulose or calcium hydrogen phosphate); lubricants (e.g. magnesium stearate, talc or silica); disintegrants (eg potato starch, croscarmellose or sodium starch glycollate); or wetting agents (e.g. sodium lauryl sulphate). The tablets may be coated by methods well known in the art. Liquid preparations for oral administration may take the form, of for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives, e.g. hydroxypropylmethylcellulose or hydrogenated edible fats); emulsifying agents (e.g. lecithin or acacia); non-aqueous vehicles (e.g. almond oil, oily esters, or ethyl alcohol or fractionated vegetable oils); and preservatives (e.g. methyl or propyl p-hydroxybenzoates or sorbic acid). The liquid preparations may also contain conventional buffers, flavouring, colouring and sweetening agents as appropriate.

For buccal administration the compositions may take the form of tablets or lozenges formulated in conventional manner.

The compounds of the invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents, and/or agents to adjust the tonicity of the solution. Alternatively, the active ingredient may be in powder form for reconstitution with a suitable vehicle, e.g. sterile hydrogen-free water, before use.

The compounds of the invention may also be formulated in rectal compositions such as suppositories or retention enemas, e.g. containing conventional suppository bases such as cocoa butter or other glycerides.

For administration by inhalation the compounds according to the invention are conveniently delivered in the form of an aerosol spray presentation from pressurised packs, with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount. Capsules and cartridges of e.g. gelatine for use in an inhaler or insufflator may be formulated containing a powder mix of a compound of the invention and a suitable powder base such as lactose or starch.

A proposed dose of the compounds of the invention for oral, parenteral, rectal or buccal administration to man (of average body weight e.g. about 70 kg) for the treatment of migraine is 0.1 to 100 mg of the active ingredient per unit dose which could be administered, for example 1 to 4 times per day. It will be appreciated that it may be necessary to make routine variations to the dosage depending on the age and weight of the patient as well as the severity of the condition to be treated.

For oral administration a unit dose will preferably contain from 2 to 50 mg of the active ingredient. A unit dose for parenteral administration will preferably contain 0.2 to 5 mg of the active ingredient.

Aerosol formulations are preferably arranged so that each metered dose or "puff" delivered from a pressurised aerosol contains 0.2 mg to 2 mg, of a compound of the invention, and each dose administered via capsules and cartridges in an insufflator or an inhaler contains 0.2 mg to 20 mg of a compound of the invention. The overall daily dose by inhalation will be within the range 1 mg to 100 mg. Administration may be several times daily for example from 2 to 8 times, giving for example 1, 2 or 3 doses each time.

The compounds of the invention may, if desired, be administered in combination with one or more other therapeutic agents, such as analgesics, anti-inflammatory agents and anti-nauseants.

According to another aspect of the invention, compounds of general formula (I) and their physiologically acceptable salts and solvates (e.g. hydrates) may be prepared by the general methods outlined hereinafter. In the following processes, $R_1$, $R_2$, $R_3$, $R_4$, A and Alk are as defined for the general formula (I) unless otherwise specified.

According to a general process (A), compounds of general formula (I) may be prepared by cyclisation of compounds of general formula (II):

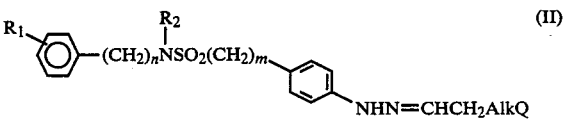

wherein Q is the group $NR_3R_4$ or a protected derivative thereof or a leaving group such as a halogen atom (e.g. chlorine or bromine), or an acyloxy group (which may be derived from a carboxylic or sulphonic acid), such as an acetoxy, chloroacetoxy, dichloroacetoxy, trifluoroacetoxy, p-nitrobenzoyloxy, p-toluene-sulphonyloxy or methanesulphonyloxy group.

The reaction may conveniently be effected in aqueous or non-aqueous reaction media, and at temperatures of from 20° to 200° C., preferably 50° to 125° C.

Particularly convenient embodiments of the process are described below.

When Q is the group $NR_3R_4$ (or a protected derivative thereof) the process is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in "Reagents for Organic Synthesis", (Fieser and Fieser, John Wiley and Sons 1967).

Alternatively the cyclisation may be carried out in an aqueous or non-aqueous reaction medium, in the presence of an acid catalyst. When an aqueous medium is employed this may be an aqueous organic solvent such as an aqueous alcohol (e.g. methanol, ethanol or isopropanol) as well as mixtures of such solvents and the acid catalyst may be, for example, an inorganic acid such as concentrated hydrochloric or sulphuric acid, or an organic acid such as acetic acid. (In some cases the acid catalyst may also act as the reaction solvent). In an anhydrous reaction medium, which may comprise one or more alcohols or ethers (eg as previously described) or esters (eg ethyl acetate), the acid catalyst will generally be a Lewis acid such as boron trifluoride, zinc chloride or magnesium chloride.

When Q is a leaving group, such as a chlorine or bromine atom, the reaction may be effected in an aqueous organic solvent, such as an aqueous alcohol (e.g. methanol, ethanol or isopropanol) or an aqueous ether (e.g. dioxan or tetrahydrofuran), in the absence of an acid catalyst, conveniently at a temperature of from 20° to 200° C., preferably 50° to 125° C. This process results in the formation of a compound of general formula (I) wherein $R_3$ and $R_4$ are both hydrogen atoms.

According to a particular embodiment of this process, compounds of general formula (I) may be prepared directly by the reaction of a compound of general formula (III):

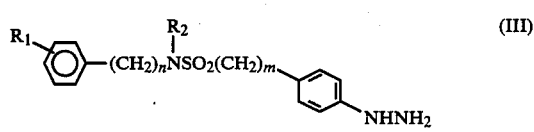

or a salt (e.g. the hydrochloride) thereof, with a compound of formula (IV):

$$OHCCH_2AlkQ \qquad (IV)$$

(where Q is as previously defined) or a salt or protected derivative thereof (such as an acetal, for example, a dialkyl or cyclic acetal e.g. formed with an appropriate alkyl orthoformate or diol or protected as a bisulphite addition complex), using the appropriate conditions as just described for the cyclisation of a compound of general formula (II) (The Fischer-Indole Synthesis, B. Robinson, p 488—Wiley 1982). In this embodiment compounds of general formula (II) may be formed as intermediates and may either be isolated prior to cyclisation or reacted in situ to form the desired compounds of general formula (I).

Compounds of general formula (II) may, if desired, be isolated as intermediates by reacting a compound of formula (III), or a salt or protected derivative thereof with a compound of formula (IV) or a salt or protected derivative thereof, in a suitable solvent, such as an aqueous alcohol (e.g. methanol) or an aqueous ether (e.g. dioxan) and at a temperature of, for example, from 20° to 30° C. If an acetal of a compound of formula (IV) is used it may be necessary to carry out the reaction in the presence of an acid (for example, acetic or hydrochloric acid).

The compounds of general formula (III) are novel compounds and form a further aspect of this invention. The compounds of general formula (III) may be prepared using conventional methods for preparing a hydrazine, for example reduction of the corresponding nitro compound to form the amino derivative, by catalytic hydrogenation, followed by reaction with sodium nitrite in the presence of a mineral acid (e.g. hydrochloric acid) to form a diazonium salt which is then reduced, e.g. with stannous chloride, to the desired hydrazine of formula (III).

A further general process (B) for preparing compounds of general formula (I) comprises reacting a compound of general formula (V):

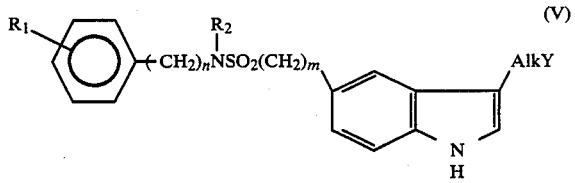

(V)

(wherein Y is a readily displaceable group)
or a protected derivative thereof, with a compound of formula $R_3R_4NH$.

This displacement reaction may conveniently be carried out on those compounds of general formula (V) wherein the substituent group Y is a halogen atom (e.g. chlorine, bromine or iodine) or a group $OR_6$ where $OR_6$ is, for example, an acyloxy group (which may be derived from a carboxylic or sulphonic acid) such as an acetoxy, chloroacetoxy, dichloroacetoxy, trifluoroacetoxy, p-nitrobenzoyloxy, p-toluene-sulphonyloxy or methanesulphonyloxy group.

The displacement reaction may conveniently be effected in an inert organic solvent (optionally in the presence of water), examples of which include alcohols, e.g. ethanol; cyclic ethers, e.g. dioxan or tetrahydrofuran; acyclic ethers, e.g. diethylether; esters e.g. ethyl acetate; amides e.g. N,N-dimethylformamide; and ketones e.g. acetone, methylethylketone or methylisobutylketone. The process may be carried out at a temperature of, for example, $-10°$ to $+150°$ C., preferably 20° to 50° C.

The compounds of formula (V) wherein Y is a halogen atom may be prepared by reacting a hydrazine of formula (III) with an aldehyde (or a protected derivative thereof) of formula (IV) in which Q is a halogen atom, in an aqueous alcohol (e.g. methanol) or an aqueous ether (e.g. dioxan) containing an acid (e.g. acetic or hydrochloric acid) or by reacting a compound of general formula (V) wherein Y is a hydroxy group with the appropriate phosphorus trihalide or with N-bromosuccinimide and triphenylphosphine in tetrahydrofuran. The intermediate alcohol, wherein Y is a hydroxy group, may also be used to prepare compounds of formula (V), wherein Y is a group $OR_6$, by acylation with the appropriate activated species (e.g. an anhydride or sulphonyl chloride) using conventional techniques. The intermediate alcohol may be prepared by cyclisation of a compound of formula (II) wherein Q is a hydroxyl group (or a protected derivative thereof) under standard conditions.

Compounds of general formula (I) may also be prepared by another general process (C) involving reduction of a compound of general formula (VI):

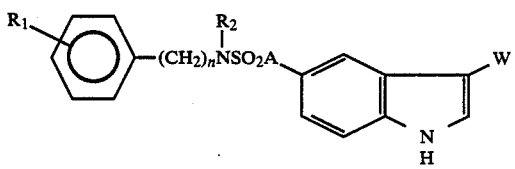

(VI)

wherein W is a group capable of being reduced to give the required $AlkNR_3R_4$ group or to give a protected derivative of the $AlkNR_3R_4$ group, and A represents the group $-(CH_2)_m-$ or a group capable of being reduced to form the group $-(CH_2)_m-$ or a salt or protected derivative thereof.

Groups A which may be reduced to give the required group $-(CH_2)_m-$ include corresponding unsaturated groups such as $C_{2-5}$-alkenyl groups.

The required Alk and $NR_3R_4$ groups may be formed by reduction steps which take place separately or together in any appropriate manner.

Groups which may be reduced to the group Alk include corresponding unsaturated groups and corresponding groups containing one or more hydroxyl groups or carbonyl functions.

Groups which may be reduced to the group $NR_3R_4$ include nitro, azido, hydroxyimino, nitrile and amide groups.

Examples of groups represented by the substituent group W thus include $TNO_2$ (where T is Alk or an alkenyl group corresponding to the group Alk); $AlkN_3$; $AlkNR_3COR_4'$; $-COCONR_3R_4$; $(CHR_7)_xCHR_8CN$; $CHR_8COZ$; $(CHR_7)_xCR_8=NOH$; $CH(OH)CHR_8NR_3R_4$; $COCHR_8Z$ (where $R_7$ and $R_8$ which may be the same or different, each represents a hydrogen atom or a $C_{1-3}$ alkyl group, Z is an azido group $N_3$ or the group $NR_3R_4$ or a protected derivative thereof, x is zero or 1 and $R_4'$ is hydrogen or a group such that $-CH_2R_4'$ is the group $R_4$ or $R_4'$ is the group $OR_c$ where $R_c$ is an alkyl or an aralkyl group).

Groups which may be reduced to the group $NR_3R_4$ wherein $R_3$ and $R_4$ are both hydrogen include nitro, azido, hydroxyimino and nitrile groups. Reduction of a nitrile group yields the group $CH_2NH_2$ and thus provides a methylene group of the group Alk.

A compound of general formula (I) where $R_4$ is a hydrogen atom, may also be prepared by reduction of a corresponding compound of general formula (I) wherein $R_4$ is a benzyl group, for example with hydrogen in the presence of a catalyst e.g. 10% palladium on carbon.

The required $NR_3R_4$ group wherein $R_3$ and/or $R_4$ are other than hydrogen may be prepared by reduction of a nitrile $(CHR_7)_xCHR_8CN$ or an aldehyde $(CHR_7)_xCHR_8CHO$ (where $R_7$, $R_8$ and x are as previously defined) in the presence of an amine, $R_3R_4NH$.

A particularly suitable method for preparing a compound of formula (I) wherein $R_3$ and/or $R_4$ is other than hydrogen, is reductive alkylation of the corresponding compound wherein $R_3$ and/or $R_4$ represents hydrogen, with an appropriate aldehyde or a ketone (e.g. formaldehyde or acetone) in the presence of a suitable reducing agent. In some instances the aldehyde may be condensed with the primary amine and the intermediate thus formed may subsequently be reduced using a suitable reducing agent.

The required $NR_3R_4$ groups wherein $R_3$ and/or $R_4$ are other than hydrogen may also be prepared by reduction of a corresponding amide, for example, $AlkN-R_3-COR_4'$ (where $R_4'$ is as previously defined).

The reduction may be effected by conventional methods, for example by catalytic hydrogenation or using a reducing agent such as an alkali metal or alkaline earth metal borohydride or cyanoborohydride, or a metal hydride. The reduction may conveniently be effected in an organic reaction medium which may comprise one or more solvents. Suitable solvents include alcohols e.g. ethanol or propanol; cyclic ethers e.g. dioxan or tetrahydrofuran; acyclic ethers e.g. diethylether; amides e.g. dimethylformamide; and esters e.g. ethyl acetate.

It will be appreciated that the choice of reducing agent and reaction conditions will be dependent on the nature of the groups W and A, as well as other groups already present in the molecule.

Suitable reducing agents which may be used in the above process for the reduction of compounds of formula (VI) wherein W represents, for example, the groups $TNO_2$, $AlkN_3$, $(CHR_7)_xCHR_8CN$, $(CHR_7)_xCR_8=NOH$ or $CH(OH)CHP_8-NR_3R_4$ (where T, $R_4'$, $R_7$ and $R_8$ and x are as previously defined) include hydrogen in the presence of a metal catalyst, for example Raney Nickel or a nobel metal catalyst such as platinum, platinum oxide, palladium or rhodium, which may be supported, for example, on charcoal, kieselguhr or alumina. In the case of Raney Nickel, hydrazine may also be used as the source of hydrogen. This process may conveniently be carried out in a solvent such as an alcohol e.g. ethanol; an ether, e.g. dioxan or tetrahydrofuran an amide, e.g. dimethylformamide; or an ester e.g. ethyl acetate, and at a temperature of from $-10°$ to $+50°$ C., preferably $-5°$ to $+30°$ C.

The reduction process may also be effected on compounds of general formula (VI) wherein W represents, for example, the groups $TNO_2$, $CH(OH)CHR_8NR_3R_4$ or $COCHR_8$ (where T, $R_8$ and Z are as previously defined), using an alkali metal or alkaline earth metal borohydride or cyanoborohydride e.g. sodium or calcium borohydride or cyanoborohydride which process may conveniently be carried out in an alcohol such as propanol or ethanol and at a temperature of from $10°$ to $100°$ C., preferably $50°$ to $100°$ C. In some instances the reduction using a borohydride may be carried out in the presence of cobaltous chloride.

Reduction of compounds of general formula (VI) wherein W represents, for example, the groups $TNO_2$, $AlkN_3$, $AlkNR_3COR_4'$, $CHR_8COZ$, $(CHR_7)_xCR_8=NOH$, $CH(OH)CHR_8-NR_3R_4$, $-CO-CONR_3R_4$ and $COCHR_8Z$ (wherein T, $T_4'$, $R_7$ and $R_8$, Z and x are as previously defined) may also be carried out using diborane or a metal hydride such as lithium aluminium hydride. This process may be carried out in a solvent, for example, an ether such as tetrahydrofuran, and conveniently at a temperature of from $-10°$ to $+100°$ C., preferably $50°$ to $100°$ C.

A particular embodiment of general process (C) includes the reduction of a compound of general formula (VI) wherein W is the group $CHR_8CN$, for example, by catalytic reduction with hydrogen in the presence of a catalyst such as palladium on charcoal or rhodium on alumina, optionally in the presence of an amine $HNR_3R_4$, or, to produce a compound wherein $R_3$ and $R_4$ are both hydrogen atoms, using lithium aluminium hydride in the absence of an amine.

Suitable reducing agents which may be used in the reduction of the group A include hydrogen in the presence of a metal catalyst. Appropriate metal catalysts and conditions for the process are as described for the reduction of the group W.

The starting materials or intermediate compounds of general formula (VI) may be prepared by analogous methods to those described in U.K. Published Patent Application No. 2035310 and "A Chemistry of Heterocyclic Compounds—Indoles Part II" Chapter VI edited by W. J. Houlihan (1972) Wiley Interscience, New York.

A compound of general formula (VI) wherein W is the gropu $AlkNHCOR_4'$ may be prepared by acylation of the corresponding unsubstituted amine using conventional techniques.

The Fischer-indole cyclisation process may be employed to prepare a compound of general formula (VI) wherein W is the group $(CHR_7)_xCHR_8CN$ or $CHR_7CHR_8NO_2$ in conventional manner.

A compound of formula (VI) wherein A is an alkenyl group containing 2 to 5 carbon atoms may be prepared by reacting a corresponding 5-halo indole of general formula (VII)

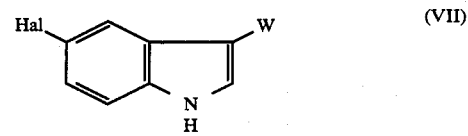

(wherein W is as defined for general formula (VI) and Hal is a halogen atom eg bromine or iodine) with an appropriate alkene of formula

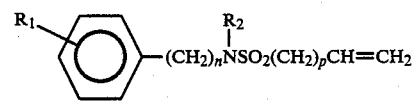

(wherein p represents zero or 1 to 3) in the presence of a catalyst such as a palladium (II) salt, for example the acetate and a phosphine e.g. triphenylphosphine or tri-o-tolylphosphine, together with a tertiary nitrogen base such as triethylamine or tri-n-butylamine. The reaction may conveniently be effected in a solvent, eg acetonitrile, methanol or dimethylformamide, and at a temperature of from $75°$ to $160°$ C. Alternatively, compounds of formula (VI) may be prepared by reaction of an appropriate indole-5-carboxaldehyde of general formula (VIII):

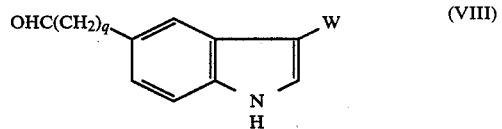

(wherein W is defined as for general formula (VI) and q is an integer from 1 to 4) with, for example, a suitable dialkylphosponate, using standard conditions.

Compounds of general formula (I) may be prepared by another general process (D) which comprises reacting an indole of general formula (IX)

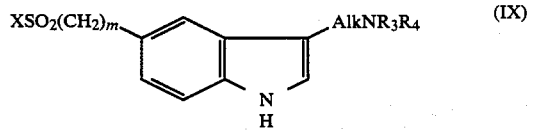

wherein X represents a leaving group with an amine of general formula (X):

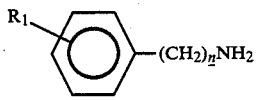

Examples of suitable leaving groups X in the compound of general formula (IX) include a halogen atom (eg a fluorine, chlorine or bromine atom) or a group $OR_9$, wherein $R_9$ represents a hydrocarbyl group such as an aryl group, e.g. phenyl. The aryl groups may be unsubstituted or substituted by one or more substituents such as halogen atoms; or nitro; cyano; amino; alkyl eg methyl; alkoxy eg methoxy; acyl, eg acetyl and alkoxycarbonyl eg ethoxycarbonyl groups. The leaving group represented by X is preferably a phenoxy group.

The reaction is conveniently carried out in the presence of a solvent and may be effected in an aqueous or non-aqueous reaction medium.

The reaction medium may thus comprise one or more organic solvents, such as ethers, e.g. dioxan or tetrahydrofuran; amides e.g. N,N-dimethylformamide or N-methylpyrrolidone; alcohols e.g. methanol or ethanol; esters e.g. ethyl acetate; nitriles e.g. acetonitrile; halogenated hydrocarbons e.g. dichloromethane; and tertiary amines e.g. triethylamine or pyridine, optionally in the presence of water. In some cases the amine of formula (X) may itself serve as the solvent.

If desired the aminolysis may be effected in the presence of a base, such as a tertiary amine (e.g. triethylamine or pyridine); an alkoxide (e.g. sodium t-butoxide) or a hydride (e.g. sodium hydride).

The reaction may conveniently be effected at a temperature of from $-20°$ C. to $+150°$ C.

The starting materials of general formula (IX) wherein X represents a group $OR_9$ may be prepared, for example by reduction of a compound of general formula (XI):

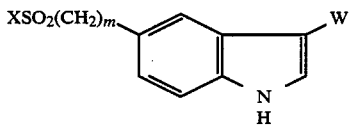

(wherein W is as defined for general formula (VI)) or a salt or protected derivative thereof.

The reduction may be carried out in analogous manner to the general process (C) and examples of suitable groups W and details of reaction conditions are given in connection with the general process (C).

A compound of formula (IX) wherein X represents a halogen atom may be prepared, for example by reacting the corresponding sulphonic acid derivative or a salt thereof with a halogenating agent such as a phosphorus halide or oxyhalide in an inert organic solvent e.g. phosphorus pentachloride in dichloromethane. A sulphonic acid of formula (IX) where X is OH, may be prepared for example by acid or base catalysed hydrolysis of an ester of formula (IX) (i.e. a compound wherein X represents the group $OR_9$).

Compounds of general formula (XI) may be prepared by analogous methods to those described in U.K. Published Patent Application No. 2035310 and "A Chemistry of Heterocyclic Compounds—Indoles Part II" Chapter VI edited by W. J. Hamilton (1972) Wiley Interscience, New York, as well as U.K. Published Patent Application No. 2124210A.

According to a further general process (E) a compound of formula (I) according to the invention or a salt or protected derivative thereof may be converted into another compound of the invention using conventional procedures.

For example, a compound of general formula (I) wherein one or both of $R_3$ and $R_4$ are alkyl or propenyl groups may be prepared from the corresponding compounds of formula (I) wherein one or both or $R_3$ and $R_4$ represent hydrogen atoms, by reaction with a suitable alkylating agent such as a compound of formula $R_xL$ where $R_x$ represents the desired $R_3$ or $R_4$ group and L represents a leaving group such as a halogen atom or a tosylate group, or a sulphate $(R_x)_2SO_4$. Thus, the alkylating agent may be for example an alkyl halide (e.g. methyl or ethyl iodide), alkyl tosylate (e.g. methyl tosylate) or dialkylsulphate (e.g. dimethylsulphate). The alkylation reaction is conveniently carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides, such as sodium or potassium hydride, alkali metal amides, such as sodium amide, alkali metal carbonates, such as sodium carbonate and alkali metal alkoxides such as sodium or potassium methoxide, ethoxide or t-butoxide. Where an alkyl halide is employed as the alkylating agent the reaction may also be carried out in the presence of an acid scavenger such as propylene or ethylene oxide. A catalyst such as tetrabutylammonium fluoride may also be employed. The reaction may conveniently be effected at a temperature of $-20°$ C. to $+100°$ C.

According to another general process (F), a compound of general formula (I) according to the invention, or a salt thereof may be prepared by subjecting a protected derivative of general formula (I) or a salt thereof to reaction to remove the protecting group or groups.

Thus, at an earlier stage in the reaction sequence for the preparation of a compound of general formula (I) or a salt thereof it may have been necessary or desirable to protect one or more sensitive groups in the molecule to avoid undesirable side reactions. For example it may be necessary to protect the group $NR_3R_4$, wherein $R_3$ and/or $R_4$ represents hydrogen, by protonation or with a group easily removable at the end of the reaction sequence. Such groups may include, for example, aralkyl groups, such as benzyl, diphenylmethyl or triphenylmethyl; or acyl groups such as N-benzyloxycarbonyl or t-butoxycarbonyl or phthaloyl.

In some cases, it may also be desirable to protect the indole nitrogen with, for example, an aralkyl group such as benzyl.

Subsequent cleavage of the protecting group or groups may be achieved by conventional procedures. Thus an aralkyl group such as benzyl, may be cleaved by hydrogenolysis in the presence of a catalyst (e.g. palladium on charcoal) or sodium and liquid ammonia; an acyl group such as N-benzyloyxcarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

As will be appreciated, in some of the general processes (A) to (E) described previously it may be necessary or desirable to protect any sensitive groups in the molecule as just described. Thus, a reaction step involving deprotection of a protected derivative of general formula (I) or a salt thereof may be carried out subsequent to any of the previously described processes (A) to (E).

Thus, according to a further aspect of the invention, the following reactions (G) in any appropriate sequence may if necessary and/or desired be carried out subsequent to any of the processes (A) to (E):

(i) removal of any protecting groups; and
(ii) conversion of a compound of general formula (I) or a salt thereof into a physiologically acceptable salt or solvate (e.g. hydrate) thereof.

Where it is desired to isolate a compound of the invention as a physiologically acceptable salt, for example as an acid addition salt, this may be achieved by treating the free base of general formula (I), with an appropriate acid (e.g. succinic or hydrochloric acid) preferably with an equivalent amount in a suitable solvent (e.g. aqueous ethanol).

The starting materials or intermediate compounds for the preparation of the compounds according to this invention may be prepared by conventional methods analogous to those described in U.K. Published Patent Application No. 2035310.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced either before or after cyclisation to form the indole nucleus. It should therefore be appreciated that in such multi-stage processes, the sequence of reactions should be chosen in order that the reaction conditions do not affect groups present in the molecule with are desired in the final product.

The invention is further illustrated by the following examples. All temperatures are in °C. 'Hyflo' is a filtration aid. Chromatography was carried out either in the conventional manner using silica gel (Merck, Kieselgel 60, Art. 7734) or by 'flash' chromatography (W. C. Still and A. Mitra, J. Org. Chem. 2923, 43, 1978) on silica (Merck 9385) and thin layer chromatography (t.l.c.), on silica (Macherly-Nagel, Polygram) except where otherwise stated. The following abbreviations define the eluent used for chromatography and t.l.c.

(A) Methylene chloride-ethanol—0.88 ammonia 100:8:1
(B) Methylene chloride-ethanol—0.88 ammonia 20:8:1
(C) Methylene chloride-ethanol—0.88 ammonia 60:8:1
(D) Methylene chloride-ethanol—0.88 ammonia 50:8:1
(E) Ether
(F) Methylene chloride-ethanol—0.88 ammonia 25:8:1
(G) Ether-cyclohexane 1:1

Intermediates were routinely checked for purity by t.l.c. employing u.v. light for detection and spray reagents such as potassium permanganate ($KMnO_4$). In addition indolic intermediates were detected by spraying with aqueous ceric sulphate ($Ce^{IV}$) and tryptamines by spraying with a solution of iodoplatinic acid (IPA) or ceric sulphate.

Proton ($^1H$) nuclear magnetic resonance (n.m.r.) spectra were obtained either at 90 MHz using a Varian EM 390 instrument or at 250 MHz using a Bruker AM or WM 250 instrument. s=singlet, d=doublet, t=triplet and m=multiplet.

Preparation 1

Phenyl 4-aminobenzenemethanesulphonate hydrochloride

A solution of phenyl 4-nitrobenzenemethanesulphonate (1.6 g) in ethyl acetate (200 ml) and concentrated hydrochloric acid (1 ml) was hydrogenated over prereduced 5% palladium oxide on charcoal (50% aqueous paste 0.4 g) in ethanol (10 ml) at atmospheric pressure and temperature. The catalyst was filtered off and the filtrate concentrated to give the title compound as a solid (1.55 g). A small sample (0.2 g) was crystallized from isopropyl acetate (10 ml) and a few drops of methanol to give analytically pure material (70 mg) m.p. 147°–148°.

Preparation 2

Phenyl 4-hydrazinobenzenemethanesulphonate hydrochloride

To a thick suspension of the product of Preparation 1 (1.5 g) in water (10 ml) and conc. hydrochloric acid (10 ml) was added a solution of sodium nitrite (0.35 g) in water (2 ml) keeping the temperature below $-2°$. More water (5 ml) was added to the resulting suspension and the cloudy solution added to a solution of tin (II) chloride dihydrate (5.6 g) in conc. hydrochloric acid (10 ml) keeping the temperature below $-2°$. The resulting suspension was stirred at room temp. for 1 h, then the precipitate was filtered off, washed with ether (200 ml) and dried in vacuo (45°; 24 h) to give a solid (1 g). A sample (0.1 g) was crystallised from isopropanol (10 ml)/methanol (2 ml) to give the title compound as a powder (30 mg) m.p. 148°–149°.

Preparation 3

Phenyl 4-[2-(3-cyano-1-propylidene)hydrazino]benzenemethanesulphonate, compound with water (40:1)

A solution of the product of Preparation 2 (1 g) and 3-cyanopropanal dimethylacetal (0.5 g) in water (20 ml) was treated with dilute hydrochloric acid (2N; 5 drops) and stirred for 16 h at room temp. The resulting solid was filtered off, washed with water (20 ml), ether (20 ml) and dried in vacuo at 20° for 2 h to give the title compound (0.9 g) m.p. 95°–96°.

Analysis Found: C, 58.9; H, 4.9; N, 11.8. $C_{17}H_{17}N_3O_3S.0.02H_2O$ requires C, 59.3; H, 5.0; N, 12.2%.

Preparation 4

Phenyl 3-(cyanomethyl)-1H-indole-5-methanesulphonate

A suspension of the product of Preparation 3 (0.8 g) in polyphosphate ester (PPE) (8 g) and chloroform (16 ml) was heated at reflux for 5 min., and then poured onto ice (50 g). The resulting suspension was stirred with ice for 20 min., then extracted with chloroform (3×20 ml). The organic extracts were washed with sodium bicarbonate (8%; 2×20 ml), water (20 ml) and dried (MgSO$_4$). The product was purified by flash chromatography (3 cm; dia) eluting with ether, and the nitrile obtained as a solid which was triturated with ether (1 ml) and dried in vacuo at 20° to give the title compound (0.27 g) m.p. 134°–135°.

EXAMPLE 1

3-(2-Aminoethyl)-N-[(4-methoxyphenyl)methyl]-1H-indole-5-methanesulphonamide hemisuccinate (i)

3-(Cyanomethyl)-N-[(4-methoxyphenyl)methyl]-1H-indole-5-methanesulphonamide

A solution of the product of Preparation 4 (0.38 g) in p-methoxybenzylamine (1.5 ml) and pyridine (2 ml) was heated on a steam bath in a closed container for 5 h. The resulting solution was poured onto ice (20 g) and concentrated hydrochloric acid (5 ml) and extracted with ethyl acetate (4×15 ml). The combined extracts were washed with dilute sodium hydroxide (5N; 2×20 ml), dried (MgSO$_4$) and the solvent evaporated in vacuo. The resulting foam (0.3 g) was crystallised from hot isopropyl acetate (10 ml) to give the title compound (0.19 g) m.p. 144°–145°.

(ii)

3-(2-Aminoethyl)-N-[(4-methoxyphenyl)methyl]-1H-indole-5-methanesulphonamide hemisuccinate A suspension of the product of Stage (i) (0.2 g) and rhodium on alumina (5%; 0.25 g) in methanolic ammonia (15 ml) was hydrogenated at atmospheric pressure and room temperature for 5 h. The catalyst was filtered off (Hyflo), washed with ethanol (20 ml), the solvent evaporated and the residue purified by column chromatography (A) then (B) to give the tryptamine as an oil (0.19 g). A hot solution of succinic acid (35 mg) in methanol (2 ml) was added to a hot solution of the tryptamine (0.19 g) in isopropanol (10 ml) and on cooling, the title compound precipitated as a solid (0.15 g) m.p. 186°–188°.

Analysis Found: C, 58.0; H, 5.9; N, 9.1 C$_{19}$H$_{23}$N$_3$O$_3$S.0.5C$_4$H$_6$O$_4$.0.04H$_2$O requires: C, 58.2; H, 6.1; N, 9.7% N.m.r. δ(CD$_3$SOCD$_3$)2.8–3.0(4H, m, CH$_2$CH$_2$NH$_2$), 3.75(3H, s, OCH$_3$), 4.02(2H, s, CH$_2$NHSO$_2$), 4.34(2H, s, NHSO$_2$CH$_2$), 6.8–7.6(8H, m, aromatic)

EXAMPLE 2

N-[(4-Methoxyphenyl)methyl]-3-[2-(methylamino)ethyl]-1H-indole-5-methanesulphonamide hemisuccinate hydrate To prereduced 10% palladium oxide on charcoal (50% paste with water; 1 g) in ethanol (10 ml) was added a solution of the product of Example 1 Stage (i) (0.5 g) in ethanolic methylamine (25 ml; 30% w/w) and the resulting suspension was hydrogenated at atmospheric pressure and room temperature for 5 h. The catalyst was filtered off (Hyflo), washed with ethanol (100 ml), the solvent evaporated and the tryptamine purified by column chromatography (C). The tryptamine (0.35 g) was dissolved in hot isopropanol (10 ml) then treated with succinic acid (50 mg) and on cooling the title compound crystallised as a solid (0.24 g) m.p. 120°–121°.

Analysis Found: C, 57.7; H, 6.1; N, 8.7. C$_{20}$H$_{25}$N$_3$O$_3$S.0.5C$_4$H$_6$O$_4$.0.5H$_2$O.0.15C$_3$H$_8$O requires: C, 58.0; H, 6.55; N, 9.05% N.m.r. δ(CD$_3$SOCD$_3$)2.40(3H, s, NHCH$_3$), 2.89(4H, brm, CH$_2$CH$_2$NH), 3.67 (3H, s, OCH$_3$), 3.91(2H, s, CH$_2$NHSO$_2$), 4.24(2H, s, NHSO$_2$CH$_2$), 6.75–7.5(8H, m, aromatic).

EXAMPLE 3

3-[2-(Dimethylamino)ethyl]-N-[(4-methoxyphenyl)methyl]-1H-indole-5-methanesulphonamide, hemisuccinate A solution of the product of Example 1 Stage (i) (0.35 g) in ethanolic dimethylamine (20 ml; 33% w/w) was hydrogenated over prereduced 10% palladium oxide on charcoal (0.6 g; 50% paste with water) in ethanol (5 ml) for 3 h. The catalyst was removed by filtration, the filtrate concentrated and the residue chromatographed (D) to give the tryptamine as a foam (0.25 g). A hot solution of the tryptamine (0.25 g) in absolute ethanol (5 ml) was treated with succinic acid (40 mg). The resulting precipitate dissolved on adding methanol (2 ml) and the solution was cooled. The title compound crystallised as a solid (0.15 g), m.p. 200°–201°.

Analysis Found: C, 60.2; H, 6.6; N, 9.1. C$_{21}$H$_{27}$N$_3$O$_3$S.0.5C$_4$H$_6$O$_4$ Requires: C, 60.0; H, 6.6; N, 9.1%.

N.m.r. δ(CD$_3$SOCD$_3$)2.39(6H, s, NMe$_2$), 2.65–3.0(4H, m, CH$_2$CH$_2$NMe$_2$), 3.75(3H, s, OMe), 4.03(2H, d, CH$_2$NHSO$_2$), 4.33(2H, s, NHSO$_2$CH$_2$)6.95–7.6(11H, m, aromatic +NH).

EXAMPLE 4

(i)

3-(Cyanomethyl)-N-[2-(4-methoxyphenyl)ethyl]-1H-indole-5-methanesulphonamide

A solution of the product of Preparation 4 (0.6 g) and 2-(4-methoxyphenyl)ethylamine (3 ml) in pyridine (5 ml) was heated at 100°–110° under nitrogen for 6h. The resulting solution was poured onto ice (50 g) and concentrated hydrochloric acid (5 ml) and extracted with ethyl acetate (4×25 ml). The organic extracts were dried (MgSO$_4$) the solvent evaporated and the residue purified by chromatography (E). The nitrile (0.6 g) was crystallised from hot ethyl acetate (10 ml) and ether (10 ml) to give the title compound as a solid (0.23 g) m.p. 134°–135°.

(ii)

3-(2-Aminoethyl)-N-[(4-methoxyphenyl)ethyl]-1H-indole-5-methanesulphonamide hemisuccinate A solution of the product of Stage (i) (0.35 g) in methanolic ammonia (20 ml) was hydrogenated over 5% rhodium on alumina (0.4 g) for 3 h. The catalyst was filtered off (Hyflo), washed with ethanol (50 ml), and the solvent evaporated. The residue was chromatographed (D) to give the tryptamine as a foam (0.35 g). To a hot solution of the tryptamine (0.35 g) in absolute ethanol (5 ml) was added succinic acid (60 mg) in methanol (1 ml) and on cooling the title compound crystallised as a solid (0.26 g), m.p. 128°–129°.

Analysis Found: C, 59.1; H, 6.5; N, 9.3. C$_{20}$H$_{25}$N$_3$O$_3$S.0.5C$_4$H$_6$O$_4$ requires C, 59.2; H, 6.3; N, 9.4%. N.m.r. δ(CD$_3$SOCD$_3$)2.4–3.2(8H, m, CH$_2$CH$_2$NH$_2$ and CH$_2$CH$_2$NHSO$_2$), 3.67(3H, s, OMe), 4.25(2H, s, NHSO$_2$CH$_2$), 6.6–7.6(m, aromatic).

EXAMPLE 5

3-(2-Aminoethyl)-N-[(4-chlorophenyl)methyl]-1H-indole-5-methanesulphonamide, compound with creatinine, sulphuric acid, and water (1:1:1:1)

(i)
3-(Cyanomethyl)-N-[(4-chlorophenyl)methyl]-1H-indole-5-methanesulphonamide

A solution of the product of Preparation 4 (0.64 g) and p-chlorobenzylamine (5 ml) in pyridine (10 ml) was heated on a steam bath for 3 h. The resulting solution was poured onto ice (20 g) and concentrated hydrochloric acid (5 ml) and extracted with ethyl acetate (4×20 ml). The organic layer was washed with sodium hydroxide (5N; 3×20 ml) and dried (MgSO$_4$). Solvent was evaporated and the nitrile purified by column chromatography (E) to give the title compound as a foam 0.5 g. T.l.c. (A) Rf 0.6.

Analysis Found: C, 57.95; H, 4.4; N, 11.0. C$_{18}$H$_{16}$ClN$_3$O$_2$S requires C, 57.8; H, 4.3; N, 11.2%.

(ii)
3-(2-Aminoethyl)-N-[(4-chlorophenyl)methyl]-1H-indole-5-methanesulphonamide To a solution of the product of Stage (i) (0.4 g) in ethanol (20 ml) and hydrazine hydrate (4 ml) was added Raney Nickel as a slurry in water (1 spatula-full, approx. 150 mg) and the resulting suspension heated at reflux for 3 h. The catalyst was filtered off, the solvent evaporated to dryness and the residue purified by column chromatography (F). To a hot solution of the product (0.17 g) in ethanol (13 ml) and water (1.6 ml) was added a solution of creatinine and sulphuric acid (1:1, 2M, 0.22 ml) and on cooling the title compound crystallised as a solid (0.2 g), m.p. 234°–235° (Decomp.)

Analysis Found: C, 43.4; H, 5.1; N, 13.75. C$_{18}$H$_{20}$N$_3$ClO$_2$S.C$_4$H$_7$N$_3$O.H$_2$SO$_4$.H$_2$O requires C, 43.5; H, 5.15; N, 13.8%. N.m.r.

δ(CD$_3$SOCD$_3$)2.9–3.2(4H, m, CH$_2$CH$_2$NH$_2$)4.09(2H, d, CH$_2$NHSO$_2$), 4.40(2H, s, NHSO$_2$CH$_2$, 7.1–7.7(m, aromatic).

EXAMPLE 6

[3-(2-Methylamino)ethyl]-N-[(4-methylphenyl)methyl]-1H-indole-5-methanesulphonamide, compound with creatinine, sulphuric acid and water (1:1:1:1)

(i)
3-(Cyanomethyl)-N-[(4-methylphenyl)methyl]-1H-indole-5-methanesulphonamide

A solution of the product of Preparation 4 (0.57 g) and 4-methylbenzylamine (5 ml) in pyridine (5 ml) was heated at 100° under nitrogen for 16 h. The resulting solution was poured onto conc. hydrochloric acid (15 ml) and ice (25 g). The solid that precipitated was filtered off, washed with water (200 ml) and recrystallised from hot isopropyl acetate (20 ml) and then from isopropanol (5 ml) to give the product (0.2 g) a sample of which (0.1 g) was purified by flash chromatography (E) to give the title compound (0.05 g) m.p. 175°–176°.

(ii)
[3-(2-Methylamino)ethyl]-N-[(4-methylphenyl)methyl]-1H-indole-5-methanesulphonamide, compound with creatinine, sulphuric acid and water (1:1:1:1)

A solution of the product of Stage (i) (0.32 g) in ethanolic methylamine (20 ml; 33% w/w) was hydrogenated over pre-reduced 10% palladium oxide on charcoal (1g; 50% paste with water) at atmospheric pressure and room temperature for 2 days. The catalyst was filtered off (Hyflo), washed with ethanol (100 ml), and the solvent evaporated. The residue was purified by column chromatography (A) then (B). A hot solution of the product (0.125 g) in ethanol (10 ml) and water (1.2 ml) was treated with a solution of creatinine and sulphuric acid (1:1, 2M, 0.17 ml) and on cooling the title compound crystallised as a solid (0.16 g), m.p. 235°–236°.

Analysis Found: C, 48.2; H, 5.8; N, 13.9. C$_{20}$H$_{25}$N$_3$O$_2$S.C$_4$H$_7$N$_3$O.H$_2$SO$_4$.H$_2$O requires C, 48.0; H, 6.0; N, 14.0%. N.m.r. δ(0.1MDCl/D$_2$O)2.28(3H, s, ArMe), 2.65(3H, s, NHCH$_3$), 3.05-3.3(4H, m, CH$_2$CH$_2$NH), 4.07(2H, s, NHSO$_2$CH$_2$), 4.40(2H, s, CH$_2$NHSO$_2$), 7.05-7.55(8H, m, aromatic).

EXAMPLE 7

3-[2-(Ethylamino)ethyl]-N-[2-(4-methoxyphenyl)ethyl]-1H-indole-5-methanesulphonamide hemisuccinate hemihydrate A solution of the product of Example 4 Stage (i) (0.35 g) in ethanolic ethylamine (20 ml; 30% w/w) was hydrogenated over pre-reduced 10% palladium oxide on charcoal (50% paste with water, 0.6 g) in ethanol (5 ml) for 3 h. The suspension was filtered through hyflo and the filtrate was evaporated to give an oil (0.29 g). Column chromatography (A) gave the tryptamine as a foam (0.15 g). A hot solution of the tryptamine (0.15 g) in absolute ethanol was heated with succinic acid (21 mg). On cooling the title compound crystallised as a solid (0.1 g) m.p. 90°–93°.

Analysis Found C, 59.7; H, 6.6; N, 8.6. C$_{22}$H$_{29}$N$_3$O$_3$S.0.5C$_4$H$_6$O$_4$.0.005H$_2$O requires C, 59.6; H, 6.7; N, 8.7%. N.m.r. δ(CD$_3$SOCD$_3$)1.0(3H, t, NHCH$_2$CH$_3$), 2.3-3.1(10H, m, CH$_2$CH$_2$NHSO$_2$ and CH$_2$CH$_2$NHCH$_2$CH$_3$), 3.60(3H, s, OMe), 4.20(2H, s, NHSO$_2$CH$_2$), 6.6–7.5(m, aromatic).

EXAMPLE 8

3-(2-Aminoethyl)-N-[3-(4-methoxyphenyl)propyl]-1H-indole-5-methanesulphonamide hemisuccinate (i)
3-(Cyanomethyl)-N-[3-(4-methoxyphenyl)propyl]-1H-indole-5-methanesulphonamide A solution of the product of Preparation 4 (0.6 g), 4-methoxybenzenepropanamine (3 ml) and pyridine (5 ml) was heated at 100°–110° for 6 h under nitrogen. The mixture was poured into concentrated hydrochloric acid (7.5 ml) and ice (20 g) and extracted with ethyl acetate (3×50 ml). The ethyl acetate extracts were combined, dried (MgSO$_4$), filtered and evaporated to give an oil (0.7 g) which was washed with diethyl ether (3×50 ml). Column chromatography (G) gave the title compound (0.4 g) m.p. 131°–133°

(ii)
3-(2-Aminoethyl)-N-[3-(4-methoxyphenyl)propyl]-1H-indole-5-methanesulphonamide hemisuccinate A solution of the product of Stage (i) (0.35 g) in methanolic ammonia (20 ml) was hydrogenated over 5% rhodium on alumina (0.35 g) for 2h. The atmosphere of hydrogen was replaced and the mixture hydrogenated for a further 18 h. The suspension was filtered through hyflo and the filtrate concentrated in vacuo to give a foam (0.35 g) which was triturated with dichloromethane (5 ml). The resulting crystals were filtered and washed with ethyl acetate (5 ml) to give the free base (0.24 g) as crystals m.p. 110°. The base (0.24 g) was dissolved in absolute ethanol (2 ml) and treated with succinic acid (35 mg) in methanol (0.5 ml). On cooling the title compound formed as crystals (0.20 g) m.p. 189°–190°.

Analysis Found: C, 59.8; H, 6.6; N, 9.0. $C_{21}H_{27}N_3O_3S \cdot 0.5C_4H_6O_4$ requires C, 60.0; H, 6.6; N, 9.1.

N.m.r. $\delta(CD_3SOCD_3)$ 1.6–1.8(2H, m), 2.52(2H, t, $CH_2CH_2CH_2NHSO_2$), 2.8–3.05(6H, m, $CH_2NHSO_2$ and $CH_2CH_2NH$—), 3.74(3H, s, OMe), 4.36(2H, s, $NHSO_2CH_2$), 6.8–7.6 (8H, m, aromatic).

EXAMPLE 9

N-[(3-Methoxyphenyl)methyl]-3-[2-(methylamino)ethyl]-1H-indole-5-methanesulphonamide compound with succinic acid (10:6)

(i)

3-(Cyanomethyl)-N-[(3-methoxyphenyl)methyl]-1H-indole-5-methanesulphonamide

A solution of the product of Preparation 4 (0.6 g), 3-methoxybenzeneethanamine (3 ml) and pyridine (5 ml) was heated at 100°–110° under nitrogen for 24 h. The mixture was poured into conc. hydrochloric acid (7 ml) and ice (20 g) and extracted with ethyl acetate (3×250 ml). The ethyl acetate extract was dried (MgSO₄), filtered and evaporated in vacuo to give an oil which was washed with ether (3×50 ml). The residue was crystallised from ethyl acetate (10 ml) to give the title compound (0.43 g) m.p. 125°–126°.

(ii)

N-[(3-Methoxyphenyl)methyl]-3-[2-(methylamino)ethyl]-1H-indole-5-methanesulphonamide compound with succinic acid (10:6)

A solution of the product of Stage (i) (0.3 g) in ethanolic methylamine (20 ml, 30% w/w) was hydrogenated over pre-reduced 10% palladium oxide on charcoal (50% paste with water, 0.3 g) in ethanol for 24 h. The suspension was filtered through hyflo and the filtrate evaporated in vacuo to give a oil (0.3 g) which was chromatographed (A) to give the tryptamine as an oil (145 mg). This oil was dissolved in absolute ethanol (2 ml) and succinic acid (22 mg) was added. The mixture was evaporated in vacuo, the residue triturated with diethyl ether (20 ml) collected and dried (vacuum pistol, 18 h, 50°) to give the title compound (115 mg) m.p. 60° (foams).

Analysis Found: C, 58.3; H, 6.4; N, 9.0. $C_{20}H_{25}N_3O_3S \cdot 0.6C_4H_6O_4$ requires C, 58.7; H, 6.2; N, 9.2%.

N.m.r. $\delta(CD_3SOCD_3)$ 2.50(3H, s, $NHCH_3$), 2.9–3.1(4H, m, $CH_2CH_2NH_2$), 3.76(3H, s, $OCH_3$), 4.08(2H, s, $CH_2NHSO_2$), 4.36(2H, s, $NHSO_2CH_2$), 6.8–7.6(8H, m, aromatic).

EXAMPLE 10

N-[(4-Methoxyphenyl)methyl]-N-methyl-3-[2-(methylamino)ethyl]-1H-indole-5-methanesulphonamide compound with succinic acid (3:1)

(i)

3-(Cyanomethyl)-N-[(4-methoxyphenyl)methyl]-N-methyl-1H-indole-5-methanesulphonamide A solution of the product of Preparation 4 (0.6 g), 4-methoxy-N-methylbenzenemethanamine (3 ml) and pyridine (5 ml) was heated at 100°–110° under nitrogen for 24 h. The mixture was poured into conc. hydrochloric acid (7 ml) and ice (20 g) and extracted with ethyl acetate (3×250 ml). The ethyl acetate extract was dried (MgSO₄) filtered and evaporated in vacuo to give an oil which was washed with diethyl ether (3×ml) and purified by column chromatography (G) to give the title compound as a foam (0.48 g) T.l.c. (A) Rf 0.8 minor impurity at 0.7.

(ii)

N-[(4-Methoxyphenyl)methyl]-N-methyl-3-[2-(methylamino)ethyl]-1H-indole-5-methanesulphonamide compound with succinic acid (3:1)

A solution of the product of Stage (i) (0.42 g) in ethanolic methylamine (20 ml, 30% w/w) was hydrogenated over pre-reduced 10% palladium oxide on charcoal (50% paste with water 0.7 g) in ethanol (5 ml) for 18 h. The suspension was filtered through hyflo and the filtrate was evaporated in vacuo to give an oil (0.4 g). Column chromatography (A) gave the tryptamine (193 mg) which was dissolved in absolute ethanol (2 ml) and treated with a solution of succinic acid (0.28 g) in ethanol (0.5 ml). The solution was evaporated, the residue triturated with diethyl ether, filtered off and dried (vacuum pistol, 18 h, 50°) to give the title compound (120 mg) as a solid m.p. 65° (foams).

Analysis Found: C, 60.7; H, 6.7; N, 9.5. $C_{21}H_{27}N_3O_3S \cdot 0.33C_4H_6O_4$ requires C, 60.95; H, 6.6; N, 9.55%.

$\delta(CD_3SOCD_3)$ 2.42(3H, s, $NHCH_3$), 2.56(3H, s, $SO_2NCH_3$), 2.91(4H, brs, $CH_2CH_2NH$), 3.72(3H, s, $OCH_3$), 4.08(2H, s, $CH_2NHSO_2$), 4.54(2H, s, $NHSO_2CH_2$), 6.9–7.6(8H, m, aromatic).

EXAMPLE 11

N-[(2-Methoxyphenyl)methyl]-3-[2-(methylamino)ethyl]-1H-indole-5-methanesulphonamide compound with creatinine, sulphuric acid and water (10:11:11:11)

(i)

3-(Cyanomethyl)-N-[(3-methoxyphenyl)methyl]-1H-indole-5-methanesulphonamide

A solution of the product of Preparation 4 (0.6 g), o-methoxybenzeneethanamine (3 ml) and pyridine (3 ml) was heated at 100°–110° under nitrogen for 24 h. The mixture was poured into conc. hydrochloric acid (7 ml) and ice (20 g) and extracted with ethyl acetate (3×250 ml). The ethyl acetate extract was dried (MgSO₄), filtered and evaporated in vacuo to give an oil (0.9 g). The oil was washed with diethyl ether (3×50 ml) and chromatographed (G) to give the title compound (0.43 g) m.p. 106°–108°.

(ii)

N-[(2-Methoxyphenyl)methyl]-3-[2-(methylamino)ethyl]-1H-indole-5-methanesulphonamide compound with creatinine, sulphuric acid and water 10:11:11:11

A solution of the product of Stage (i) (0.3 g) in ethanolic methylamine (20 ml, 30% w/w) was hydrogenated over prereduced 10% palladium oxide on charcoal (50% paste with water, 0.3 g) in ethanol (5 ml) for 18 h. Further portions of catalyst (0.3 g and 0.5 g) were added after 18 and 36 h. The mixture was filtered through hyflo and evaporated in vacuo to give an oil (0.18 g) which was purified by column chromatography (A) The resulting oil (0.017 g) was dissolved in ethanol (1.6 ml) and filtered through hyflo. The filtrate was treated with water (0.12 ml), warmed and a solution of creatinine and sulphuric acid (2M, 1:1, 0.022 mmol) was added. The resulting mixture was cooled and the solid filtered off and dried at 60° for 18 h in vacuo to give the title compound (17 mg) m.p. 218°–220°.

Analysis Found: C, 46.0; H, 5.8; N, 13.6. $C_{20}H_{25}N_3O_3S.1.1C_4H_7N_3O.1H_2SO_4.1.1H_2O$ C, 45.8; H, 5.8; N, 13.8%.

N.m.r. δ(CD$_3$SOCD$_3$)2.63(3H, s, HNC$\underline{H}_3$), 3.03(2H, t, CH$_2$C$\underline{H}_2$NHCH$_3$), 3.21(2H, t, C$\underline{H}_2$CH$_2$NHCH$_3$3.82(3H, s, OCH$_3$), 4.12(2H, d, C$\underline{H}_2$NHSO$_2$), 4.37(2H, s, NHSO$_2$C$\underline{H}_2$), 6.9–7.6(8H, m, aromatic)

EXAMPLE 12

3-[2-(Dimethylamino)ethyl]-N-[2-(4-methoxyphenyl)ethyl]-1$\underline{H}$-indole-5-methanesulphonamide hemisuccinate hydrate A solution of Example 4 Stage (i) (0.3 g) in ethanolic dimethylamine (20 ml 30 w/w) was hydrogenated over pre-reduced 10% palladium oxide on charcoal (0.6 g, 50% paste with water) in ethanol (5 ml) for 48 h. The suspension was filtered through hyflo and the filtrate evaporated in vacuo to give an oil (0.27 g). Column chromatography (A) gave the tryptamine as an oil (176 mg). The oil (128 mg was dissolved in ethanol (10 ml) and treated with succinic acid (18 mg). A solid was collected by filtration to give the title compound (35 mg) as a powder m.p. 67°–70°.

Analysis Found: C, 58.3; H, 6.6; N, 8.3. $C_{22}H_{29}N_3O_3S.0.5C_4H_6O_4.H_2O$ C, 58.5; H, 6.9; N, 8.5%.

N.m.r. δ(CD$_3$SOCD$_3$)2.38(s, NM$\underline{e}_2$), 2.6–3.15(8H, m, C$\underline{H}_2$C$\underline{H}_2$NMe$_2$ and C$\underline{H}_2$C$\underline{H}_2$NHSO$_2$), 3.75(3H, s, OM$\underline{e}$), 4.36(2H, s, NHSO$_2$C$\underline{H}_2$), 6.8–7.6(9H, m, aromatic +NH$\underline{SO}_2$)

EXAMPLE 13

4-[[[[[3-[-2-(Dimethylamino)ethyl]-1$\underline{H}$-indol-5-yl]methyl]sulphonyl]amino]methyl]benzamide oxalate hydrate (i) 4-(Aminomethyl)benzamide A suspension of 6-cyanobenzamide (8.80 g) in methanolic ammonia (250 ml) was hydrogenated at room temperature and pressure over rhodium on alumina (5.0 g) for 18 h. The suspension was filtered through hyflo and the filtrate evaporated to dryness and the residue recrystallised twice from ethyl acetate to give the title compound (3.5 g). m.p. 141°–145° C.

(ii) 4-[[[[[3-(Cyanomethyl)-1$\underline{H}$-indol-5-yl]methyl]sulphonyl]amino methyl]benzamide A mixture of 4-(aminoethyl)benzamide (3.0 g) and the product of Preparation 4 (1.2 g) in pyridine (10 ml) was heated at 110° for 48 h. The reaction mixture was poured into conc.HCl (25 ml) and ice (50 g). The mixture was extracted with ethyl acetate (3×100 ml). The organic extracts were combined, dried (MgSO$_4$) and evaporated to give an oil which was triturated with ether (3×100 ml) to give the title compound (0.6 g) m.p. 202°–206°.

(iii)

4-[[[[[3-[2-(Dimethylamino)ethyl]-1$\underline{H}$-indol-5-yl]methyl]sulphonyl]amino]methyl]benzamide oxalate A suspension of the product of stage (ii) (0.3 g) in methanol (30 ml) was treated with dimethylamine in ethanol 33% w/w, 20 ml) and then hydrogenated over prereduced palladium oxide on charcoal (10%, 0.6 g) at room temperature and pressure for 18 h. The catalyst was filtered off (hyflo) and the reaction mixture concentrated in vacuo to give a foam (0.15 g) which was purified by flash chromatography (D). The product (0.09 g) in hot absolute ethanol (10 ml) was treated with oxalic acid (0.019 g) in absolute ethanol (1 ml). Cooling deposited the title compound (0.043 g) m.p. 115°–120°.

Analysis C, 53.2; N, 5.5; N, 10.8. $C_{21}H_{26}N_4OS.C_2H_2O_4.0.67H_2O$ C,53.5; H, 5.7; N, 10.8%

N.m.r. δ(CD$_3$SOCD$_3$)2.74(6H, s, NM$\underline{e}_2$)3.0–3.2(4H, m, CH$_2$C$\underline{H}_2$NMe$_2$), 4.18(2H, d, C$\underline{H}_2$NSO$_2$)4.22(2H, s, C$\underline{H}_2$SO$_2$NH),7.0–8.1(11H, m, aromatic+SO$_2$N$\underline{H}$+CONH$_2$)11.04(1H, br s, indole-N$\underline{H}$)

The following examples illustrate pharmaceutical formulations according to the invention, containing 3-[2-(dimethylamino)ethyl]-N-[2-(4-methoxyphenyl)ethyl]-1$\underline{H}$-indole-5-methanesulphonamide hemisuccinate hydrate as the active ingredient. Other compounds of the invention may be formulated in a very similar manner.

TABLETS FOR ORAL ADMINISTRATION

| DIRECT COMPRESSION | |
|---|---|
| | mg/tablet |
| Active ingredient | 2.38 |
| Calcium hydrogen phosphate B.P.* | 95.12 |
| Croscarmellose sodium USP | 2.00 |
| Magnesium stearate, B.P. | 0.50 |
| Compression weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target fill weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

| CAPSULES | |
|---|---|
| | mg/capsule |
| Active ingredient | 29.50 |
| *Starch 1500 | 169.50 |
| Magnesium Stearate BP | 1.00 |

| CAPSULES | |
|---|---|
| | mg/capsule |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| SYRUP | |
|---|---|
| | mg/5 ml dose |
| Active ingredient | 29.50 |
| Buffer | |
| Flavour | |
| Colour | |
| Preservative | as required |
| Thickening agent | |
| Sweetening agent | |
| Purified Water | to 5.00 ml |

The active ingredient, buffer, flavour, colour, preservative, thickening agent and sweetening agent are dissolved in some water, the solution is adjusted to volume and mixed. The syrup produced is clarified by filtration.

| SUPPOSITORY FOR RECTAL ADMINISTRATION | |
|---|---|
| Active ingredient | 6.0 mg |
| *Witepsol H15 to | 1.0 g |

*A proprietary grade of Adeps Solidus Ph. Eur.

A suspension of the active ingredient in molten Witepsol is prepared and filled, using suitable machinery, into lg size suppository moulds.

| INJECTION FOR INTRAVENOUS ADMINISTRATION | |
|---|---|
| | mg/ml |
| Active ingredient | 1.2 mg |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

FOR INHALATION

| INHALATION CARTRIDGES | |
|---|---|
| | mg/cartridge |
| Active ingredient (micronised) | 17.8 |
| Lactose BP to | 25.00 |

The active ingredient is micronised in a fluid energy mill to a fine particle size range prior to blending with normal tabletting grade lactose in a high energy mixer. The powder blend is filled into No.3 hard gelatin capsules on a suitable encapsulating machine. The contents of the cartridges are administered using a powder inhaler such as the Glaxo Rotahaler.

We claim:

1. A compound of formula:

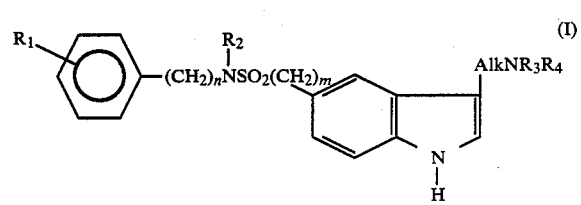

wherein
R$_1$ which may be in the ortho, meta or para position, represents a halogen atom, C$_{1-3}$alkyl, C$_{1-3}$alkoxy, hydroxy, a group NR$_a$R$_b$ or CONR$_a$R$_b$, where R$_a$ and R$_b$, which may be the same or different, each represents a hydrogen atom, C$_{1-3}$ alkyl, C$_{3-4}$alkenyl;
R$_2$ represents a hydrogen atom or a C$_{1-3}$alkyl group;
R$_3$ and R$_4$, which may be the same or different, each represents a hydrogen atom, C$_{1-3}$alkyl, propenyl or R$_3$ and R$_4$ together form a benzylidene group; Alk represents an alkylene chain containing two or three carbon atoms which may be unsubstituted or substituted by not more than two C$_{1-3}$alkyl groups; and
n and m which may be the same or different, each represents an integer from 1 to 4 or n may be zero; and physiologically acceptable salts and hydrate thereof.

2. A compound of formula (I) or a physiologically acceptable salt or hydrate thereof according to claim 1, wherein in the formula (I) R$_1$ represents a halogen atom, a C$_{1-3}$ alkyl or C$_{1-3}$ alkoxy group, or a group NR$_a$R$_b$ or CONR$_a$R$_b$, in which R$_a$ and R$_b$, which may be the same or different each represent a hydrogen atom or a C$_{1-3}$ alkyl group.

3. A compound of formula (I) or a physiologically acceptable salt or hydrate thereof according to claim 1, wherein in the formula (I) R$_2$ represents a hydrogen atom.

4. A compound of formula (I) or a physiologically acceptable salt or hydrate thereof according to claim 1, wherein in the formula (I) R$_3$ and R$_4$ each represents a hydrogen atom or a C$_{1-3}$ alkyl or propenyl group.

5. A compound of formula (I) or a physiologically acceptable salt or hydrate thereof according to claim 1, wherein in the formula (I) Alk is an unsubstituted alkylene chain containing two carbon atoms.

6. A compound of the formula (Ia)

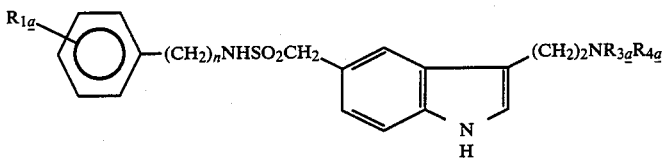

(Ia)

wherein
$R_{1a}$ (which may be in the ortho, meta or para position) represents a $C_{1-3}$ alkoxy or a $C_{1-3}$ alkyl group;
$R_{3a}$ and $R_{4a}$, which may be the same or different each represents a hydrogen atom or a $C_{1-3}$ alkyl group; and
n is an integer from 1 to 4,
and physiologically acceptable salts and solvates thereof.

7. A compound selected from
3-(2-aminoethyl)-N-[(4-methoxyphenyl)methyl]1H-indole-5-methanesulphonamide;
N-[(4-methoxyphenyl)methyl]-3-[2-(methylamino)ethyl]-1H-indole-5-methanesulphonamide;
3-(2-aminoethyl)-N-[(4-methoxyphenyl)ethyl]-1H-indole-5-methanesulphonamide;
3-(2-aminoethyl)-N-[3-(4-methoxyphenyl)propyl]-1H-indole-5-methanesulphonamide; and
3-[2-(dimethylamino)ethyl]-N-[2-(4-methoxyphenyl)ethyl]-1H-indole-5-methanesulphonamide; and the physiologically acceptable salts and hydrate thereof.

8. A pharmaceutical composition which comprises an effective amount of at least one compound of formula (I) of claim 1 or a physiologically acceptable salt or solvate thereof together with a physiologically acceptable carrier therefor for the treatment of pain originating from dilatation of the cranial vasculature.

9. A method for the treatment of pain resulting from dilatation of the cranial vasculature which comprises administering to a patient an effective amount of a compound as claimed in claim 1 to relieve said pain.

* * * * *